United States Patent [19]

Oshima et al.

[11] 4,443,548
[45] Apr. 17, 1984

[54] PROCESS FOR PREPARING L-α-METHYLPHENYL ALANINES

[75] Inventors: Tokio Oshima; Tomio Kimura; Tetsuo Omata; Noritada Iwamoto, all of Ube, Japan

[73] Assignee: Ube Industries, Ltd., Yamaguchi, Japan

[21] Appl. No.: 376,236

[22] Filed: May 7, 1982

[30] Foreign Application Priority Data

May 14, 1981 [JP]  Japan ................................ 56-71397

[51] Int. Cl.³ .................... C07B 19/02; C12P 13/22
[52] U.S. Cl. ................................ 435/280; 435/108
[58] Field of Search ............. 435/108, 280, 123–126, 435/228

[56] References Cited

U.S. PATENT DOCUMENTS 4,260,684  4/1981  Schutt ................................ 435/280
4,366,250  12/1982  Jallageas et al. .................... 435/280

OTHER PUBLICATIONS

Derwent Abstract 77260A/43 of Japanese Patent 53-107,481 (9/19/78).
Methods in Enzymology vol. XVII B pp. 652–656 (1971).
Chemical Abstracts vol. 62: 15998e (1965).

Primary Examiner—Lionel M. Shapiro
Attorney, Agent, or Firm—Burgess, Ryan & Wayne

[57] ABSTRACT

Biochemical optical resolution of DL-α-methylphenyl alanines in which DL-α-methylphenyl alanine amides are interacted with the culture products, or their treated products, of a microorganism capable of producing amidase is described. L-α-methylphenyl alanines having the general formula (I):

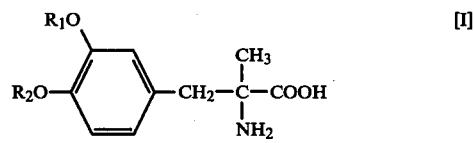

wherein $R_1$ and $R_2$ may be independently a hydrogen atom or lower alkyl groups, or $R_1$ and $R_2$ may be alkylene groups combined together to form 5 through 8-membered rings is produced by the steps of:

(a) making a DL-α-methylphenyl alanine amide having the general formula (II):

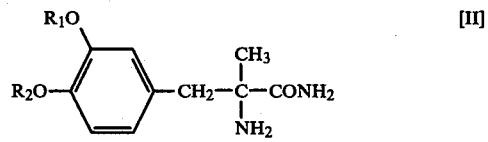

wherein $R_1$ and $R_2$ are the same as defined above, interact with the culture product of a microorganism capable of producing enzyme catalyzing the hydrolysis of L-isomer of DL-α-methylphenyl alanine amides or the treated product thereof, whereby asymmetric hydrolysis of an L-α-methylphenyl alanine amide is effected; and (b) separating the resultant L-α-methylphenyl alanines from the hydrolysis mixture.

5 Claims, No Drawings

PROCESS FOR PREPARING L-α-METHYLPHENYL ALANINES

BACKGROUND OF THE INVENTION

1. Field of the Invention

The present invention relates to a process for preparing L-α-methylphenyl alanines by biochemical asymmetric hydrolysis of DL-α-methylphenyl alanine amides, in which a microbial enzyme catalyzing a hydrolysis of L-isomer of DL-α-methylphenyl alanine amides is utilized.

2. Description of the Prior Art

It is known in the art that pharmacological activities are possessed by L-α-methylphenyl alanines, but not D-α-methylphenyl alanines. For instance, L-3,4-dihydroxy-α-methylphenyl alanine, usually referred to as "methyl dopa", is a well-known excellent hypotensor, while D-3,4-dihydroxy-α-methylphenyl alanine has no hypotensor activity. Accordingly, effective optical resolution of chemically synthesized DL-α-methylphenyl alanines is an extremely important problem to be solved in the art.

Various optical resolution methods of the racemic mixture of α-methylphenyl alanines have been heretofore proposed, including physical methods, such as diastereomer methods or fractional crystallization methods, and biochemical methods, utilizing microorganisms.

Diastereomer methods are disadvantageous in that the yield of the desired product is low, the recovery of the desired product is troublesome, the resolution agent used is expensive, and the recovery of the resolution agent is not easy.

Fractional crystallization methods are disadvantageous in that the racemic mixture is often crystallized prior to crystallization of the desired optically active product even if crystals of the desired optically active product are seeded and that both the resolution rate (%) and the crystallization reproducibility of the desired optically active product are low.

In known biochemical resolution methods, N-succinyl or N-benzoyl derivatives of DL-α-methylphenyl alanines are used as substrates for asymmetric hydrolysis by microbial enzymes. These methods are, however, disadvantageous in that the synthesis of the substrates is troublesome, the reuse of the remaining substrates (i.e., D-derivatives) is difficult, and the yield of the desired product is low.

SUMMARY OF THE INVENTION

Accordingly, an object of the present invention is to provide a biochemical method for resolution of DL-α-methylphenyl alanines eliminating the above-mentioned disadvantages in the prior arts, thereby effectively producing L-α-methylphenyl alanines.

Other objects and advantages of the present invention will be apparent from the description set forth hereinbelow.

In accordance with the present invention, there is provided a process for preparing an L-α-methylphenyl alanine having the general formula [I]:

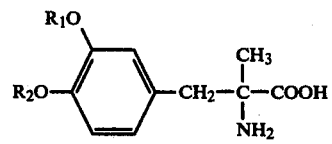

wherein $R_1$ and $R_2$ may be independently a hydrogen atom or lower alkyl group, or $R_1$ and $R_2$ may be alkylene groups combined together to form 5-through 8-membered rings, comprising the steps of:

(a) making a DL-α-methylphenyl alanine amide having the general formula [II]:

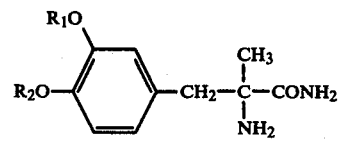

wherein $R_1$ and $R_2$ are the same as defined above, interact with the culture product of a microorganism capable of producing enzyme catalyzing the hydrolysis of L-isomer of DL-α-methylphenyl alanine amide or the treated product thereof, whereby asymmetric hydrolysis of an L-α-methylphenyl alanine amide is effected; and (b) separating the resultant L-α-methylphenyl alanines from the hydrolysis mixture.

DETAILED DESCRIPTION OF THE INVENTION

The term "the treated product" used herein means that the cells or broth separated from the cultivation mixture, or enzyme preparations including cell-free extract, crude enzyme and purified enzyme prepared from the cultivation mixture, the cells or broth, or the immobilized preparations derived from all of them.

Typical examples of the DL-α-methylphenyl alanine amides having the above-mentioned general formula [II] and usable as substrates in the present invention are as follows. It should be noted, however, that these substrates are not restrictive, but illustrative.

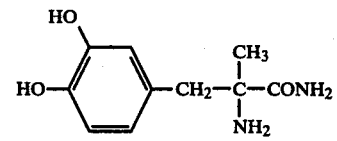

DL-3,4-dihydroxy-α-methylphenyl alanine amide

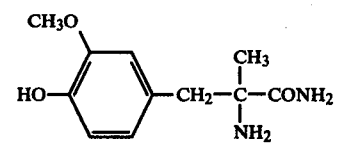

DL-4-hydroxy-3-methoxy-α-methylphenyl alanine amide

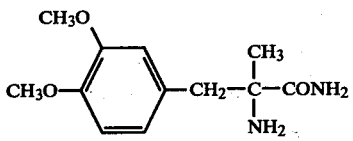

DL-3,4-dimethoxy-α-methylphenyl alanine amide

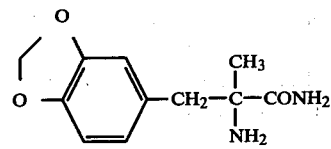

DL-3,4-methylenedioxy-α-methylphenyl alanine amide

These substrates may be readily prepared by, for example, reacting ammonium cyanide to phenylacetones to form the amino nitrile derivatives and hydrolyzing the nitrile group of the resultant amino nitrile derivatives in the presence of an acid.

The microorganisms usable in the present invention include any microorganisms which can produce enzyme catalyzing the hydrolysis of only L-isomer in a racemic mixture of DL-α-methylphenyl alanine amides, regardless of their taxonomical groups. Examples of the genus names of these microorganisms are listed in the following table, in which the typical species name of the microorganism belonging to each genus is also listed. However, it should be noted that the microorganisms which can be employed in the practice of the present invention are not limited to these specific examples. All the exemplified microorganisms are known and also readily available from the depositories of JFCC (Japanese Federation of Culture Collections of Microorganisms) such as IFO (Institute for Fermentation, Osaka, Japan) and IAM (Institute of Applied Microbiology, University of Tokyo, Tokyo, Japan), and NIHJ (National Institute of Health, Japan).

| (1) | Genus Rhizopus | IFO-4768 |
|---|---|---|
| | Rhizopus chinensis | |
| (2) | Genus Absidia | IFO-4011 |
| | Absidia orchidis | |
| (3) | Genus Aspergillus | IFO-4068 |
| | Aspergillus niger var fermentarius | |
| (4) | Genus Penicillium | IFO-5692 |
| | Penicillium frequentans | |
| (5) | Genus pullularia | IFO-4464 |
| | Pullularia pullulans | |
| (6) | Genus Fusarium | IFO-5421 |
| | Fusarium roseum | |
| (7) | Genus Gibberella | IFO-5268 |
| | Gibberella fujikuroi | |
| (8) | Genus Trichoderma | IFO-4847 |
| | Trichoderma viride | |
| (9) | Genus Gliocladium | IFO-5422 |
| | Gliocladium roseum | |
| (10) | Genus Cunninghamella | IFO-4441 |
| | Cunninghamella elegans | |
| (11) | Genus Actinomucor | IFO-4022 |
| | Actinomucor repens | |
| (12) | Genus Geotrichum | IFO-6454 |
| | Geotrichum candidum | |
| (13) | Genus Saccharomyces | IFO-0505 |
| | Saccharomyces rouxii | |
| (14) | Genus Shizosaccharomyces | IFO-0346 |
| | Shizosaccharomyces pombe | |
| (15) | Genus Pichia | IFO-0195 |
| | Pichia polimorpha | |
| (16) | Genus Hansenula | IFO-0117 |

-continued

| | | |
|---|---|---|
| | Hansenula anomala | |
| (17) | Genus Debariomyces | IFO-0023 |
| | Debariomyces hansenii | |
| (18) | Genus Nadsonia | IFO-0665 |
| | Nadsonia elongata | |
| (19) | Genus Sporobolomyces | IFO-0376 |
| | Sporobolomyces pararoseus | |
| (20) | Genus Cryptococcus | IFO-0378 |
| | Cryptococcus albidus | |
| (21) | Genus Torulopsis | IFO-0768 |
| | Torulopsis candida | |
| (22) | Genus Brettanomyces | IFO-0642 |
| | Brettanomyces anomalus | |
| (23) | Genus Candida | IFO-0396 |
| | Candida utilis | |
| (24) | Genus Tricosporon | IFO-0598 |
| | Tricosporon beigelii | |
| (25) | Genus Rhodotorula | IFO-0412 |
| | Rhodotorula minuta var texensis | |
| (26) | Genus Mycobacterium | |
| | Mycobacterium smegmatis | NIHJ-1628 |
| | Mycobacterium avium chester | IFO-3154 |
| | Mycobacterium phlei | IFO-3158 |
| (27) | Genus Nocardia | IFO-3424 |
| | Nocardia asteroides | |
| (28) | Genus Streptomyces | IFO-3356 |
| | Streptomyces griseus | |
| (29) | Genus Aerobacter | IFO-3320 |
| | Aerobacter aerogenes | |
| (30) | Genus Alcaligenes | IAM-1517 |
| | Alcaligenes viscolactis | |
| (31) | Genus Flvobacterium | IAM-1100 |
| | Flavobacterium arborescens | |
| (32) | Genus Bacillus | IFO-3026 |
| | Bacillus subtilis | |
| (33) | Genus Agrobacterium | IFO-13262 |
| | Agrobacterium tumefaciens | |
| (34) | Genus Micrococcus | IFO-3242 |
| | Micrococcus flavus | |
| (35) | Genus Sarcina | IFO-3064 |
| | Sarcina aurantiaca | |
| (36) | Genus Arthrobacter | IFO-3530 |
| | Arthrobacter simplex | |
| (37) | Genus Brevibacterium | IFO-12071 |
| | Brevibacterium ammoniagenes | |
| (38) | Genus Pseudomonas | |
| | Pseudomonas iodinum | IFO-3558 |
| | Pseudomonas fluorescens | IFO-3081 |
| (39) | Genus Lactobacillus | IFO-3322 |
| | Lactobacillus casei | |
| (40) | Genus Streptococcus | IFO-3434 |
| | Streptococcus lactis | |
| (41) | Genus Clostridium | IFO-3346 |
| | Clostridium acetobutyricum | |
| (42) | Genus Enterobacter | IFO-3317 |
| | Enterobacter aerogenes | |
| (43) | Genus Ustilago | IFO-5346 |
| | Ustilago zeae | |

Among these microorganisms, microorganisms belonging to genera Trichoderma, Nocardia, Mycobacterium, Bacillus, Rhizopus, Candida, Hansenula, Streptomyces, Aerobacter, Arthrobacter, Pseudomonas, Gibberella, Torulopsis, Enterobacter, and Ustilago are especially useful in the practice of the present invention, In the practice of the present invention, the above-mentioned microorganisms can be made to interact with the DL-α-methylphenyl alanine amides in the form of the cultivation mixture thereof, the cells or broth separated from the mixture, or enzyme preparations including cell-free extract, crude enzyme, and purified enzyme prepared from the cultivation mixture, the cells or the broth according to conventional methods. The cells, or enzyme may be immobilized on carriers in the practice of the present invention.

The enzyme which can catalyze the hydrolysis of L-isomer of DL-α-methylphenyl alanine amides is not clearly understood, but it would seem amidase, without prejudice to the invention.

Examples of the carriers usable in the present invention are natural products such as alginic acid, carrageenan, collagen, cellulose, acetylcellulose, agar, cellophane, and collodion and synthetic polymer substances such as polyacrylamide, polystyrene, polyethylene glycol, polypropylene glycol, polyurethane, and polybutadiene. The immobilization of the cells or enzyme on the carrier can be carried out in a conventional methods under moderate conditions so that the activity of the enzyme is not impaired.

The suitable reaction temperature of the asymmetric hydrolysis according to the present invention can be within the range of from 20° C. through 50° C. However, in order to minimize the decrease in the enzymatic activity, the use of the reaction temperature of from 25° C. through 40° C. is economically advantageous. The suitable reaction time of the asymmetric hydrolysis according to the present invention can be within the range of from 5 through 50 hours. However, the reaction time can be shortened by raising the reaction temperature or by increasing the amount of the enzymes used. Furthermore, the reaction can be generally carried out under a pH of 5 through 10, more preferably 7 through 9.

The amount of the microorganisms employed in the practice of the present invention is desirably in a weight ratio of from 0.01 through 2, in terms of the freeze dried cells, based on the weight of the DL-$\alpha$-methylphenyl alanine amides. In the case where the cultivation mixtures of the microorganisms, enzyme preparations prepared from the mixtures or cells, or the immobilized products thereof are employed, the amount thereof can be determined in terms of the amount of the freeze dried cells. The suitable concentration of the substrate, i.e., DL-$\alpha$-methylphenyl alanine amides in the reaction mixture is generally within the range of from 1% through 40% by weight, desirably 5% through 30% by weight.

According to the present invention, the asymmetric hydrolysis reaction is stopped after the hydrolysis of L-$\alpha$-methylphenyl alanine amides proceeds at the conversion rate of almost 100%, and then, L-$\alpha$-methylphenyl alanines and D-$\alpha$-methylphenyl alanine amides are separately isolated from the reaction mixture. This separation can be readily carried out by using any conventional separation techniques, such as fractional crystallization and solvent extraction, D-$\alpha$-methylphenyl alanine amides are not affected by the action of the microorganisms in the above-mentioned asymmetric hydrolysis and, therefore, almost all D-$\alpha$-methylphenyl alanine amides can be recovered from the racemic mixture. The D-$\alpha$-methylphenyl alanine amides thus recovered can be readily hydrolyzed by using any conventional techniques, for example, by heating in the presence of an aqueous acid or alkaline solution. The resultant D-$\alpha$-methylphenyl alanines are treated by sodium hypochlorite to form phenyl acetones, which, in turn, are again usable as starting material for the synthesis of the above-mentioned substrate.

The present invention has the advantages in that, as compared with known biochemical processes, (1) the substrates to be used can be readily prepared at a low cost, (2) the separation of the desired product from the remaining substrate (i.e., D-isomer) in the reaction mixture is not difficult and the recovered D-isomer can be used again as the starting material for the synthesis of the substrate, and (3) the optical purity and yield of the desired product are high.

EXAMPLES

The present invention will now be further illustrated by, but is by no means limited to, the following examples wherein the yield of L-$\alpha$-methylphenyl alanines is calculated from the following equation.

$$\text{Yield (\%)} = \frac{\text{moles of the resultant L-}\alpha\text{-methylphenyl alanines}}{\text{moles of the L-}\alpha\text{-methylphenyl alanine amides in the starting substrate}} \times 100$$

EXAMPLES 1 THROUGH 15

One hundred ml of a culture medium having a pH of 7.0 and containing 5% by weight of glycerol, 5% by weight of corn steep liquor, 0.5% by weight of ammonium sulfate, and 1 ml of a mixture of inorganic salts was charged into a shaking flask. The inorganic salts mixture was prepared by dissolving 20 g of $MgSO_4 \cdot 7H_2O$, 5 g of $FeSO_4 \cdot 7H_2O$, 2 g of $CaCl_2$, 0.2 g of $MnCl_2 \cdot 4H_2O$, 0.1 g of $NaMoO_4 \cdot 2H_2O$, and 0.1 g of NaCl in 1,000 ml of distilled water. After sterilizing the content of the flask, 2 loopfuls each of the microorganisms listed in Table 1 below were inoculated from an agar slant and, then, the reciprocal shaking culture (or incubation) was carried out at a temperature of 30° C. for 65 hours.

Thereafter, 2 g of DL-3,4-dimethoxy-$\alpha$-methylphenyl alanine amide was added to the flask and, then, the reciprocal shaking culture was carried out at a temperature of 30° C. for 48 hours. The cells were removed from the reaction mixture by centrifugation or filtration. The filtrate was analyzed with a high speed liquid chromatograph. Thus, the yield of 3.4-dimethoxy-$\alpha$-methylphenyl alanine thus obtained was determined.

No specific optical rotation data of L- or D-3,4-dimethoxy-$\alpha$-methylphenyl alanine were available in literatures. Accordingly, the resultant 3,4-dimethoxy-$\alpha$-methylphenyl alanine was converted to N-acetyl-3,4-dimethoxy-$\alpha$-methylphenyl alanine according to a method described in the following Example 16. From the specific optical rotation data of the N-acetyl derivatives available in literatures, it was confirmed that the 3,4-dimethoxy-$\alpha$-methylphenyl alanine obtained in each Example was L-isomer.

The results obtained in Examples 1 through 15 are shown in the following Table 1.

TABLE 1

| | | Formed L-3,4-dimethoxy-$\alpha$-methylphenyl alanine | |
|---|---|---|---|
| Example | Microorganism used | yield (%) | Specific optical rotation $[\alpha]_D$ (C = 1, $H_2O$)* |
| 1 | Enterobacter aerogenes IFO-3317 | 42 | −50° |
| 2 | Bacillus subtilis IFO-3026 | 74 | −49° |
| 3 | Candida utilis IFO-0396 | 36 | −51° |
| 4 | Rhizopus chinensis IFO-4768 | 30 | −47° |
| 5 | Trichoderma viride IFO-4847 | 28 | −46° |
| 6 | Nocardia asteroides IFO-3424 | 49 | −48° |
| 7 | Mycobacterium smegmatis NIHJ-1628 | 86 | −52° |

TABLE 1-continued

| | | Formed L-3,4-dimethoxy-α-methylphenyl alanine | |
|---|---|---|---|
| Example | Microorganism used | yield (%) | Specific optical rotation $[\alpha]_D$ (C = 1, H₂O)* |
| 8 | *Streptomyces griseus* IFO-3356 | 33 | −49° |
| 9 | *Ustilago zeae* IFO-5346 | 66 | −51° |
| 10 | *Aerobacter aerogenes* IFO-3320 | 51 | −52° |
| 11 | *Arthrobacter simplex* IFO-3530 | 23 | −49° |
| 12 | *Pseudomonas fluorescens* IFO-3081 | 94 | −53° |
| 13 | *Gibberella fujikuroi* IFO-5268 | 31 | −47° |
| 14 | *Torulopsis candida* IFO-0768 | 17 | −45° |
| 15 | *Hansenula anomala* IFO-0177 | 30 | −44° |

*Specific optical rotation of N—acetyl compound

EXAMPLE 16

From the culture mixture of Mycobacterium avium chester (IFO-3154) prepared in the same manner as in Example 1, the cells were collected by centrifugation and, then, washed twice with distilled water.

The washed cells were added to 100 ml of a 0.1 M phosphate buffer solution having a pH of 7.0 and containing 2 g of DL-3,4-dimethoxy-α-methylphenyl alanine amide. The resultant mixture was incubated at a temperature of 30° C. for 20 hours.

After completing the reaction, the cells were removed from the reaction mixture by centrifugation. The resultant reaction mixture thus obtained was analyzed by a high speed liquid chromatography. As a result, the resultant reaction mixture contained 950 mg of L-3,4-dimethoxy-α-methylphenyl alanine (yield=95%) and 1030 mg of D-3,4-dimethoxy-α-methylphenyl alanine amide.

The reaction mixture was extracted by 200 ml of benzene. Thus, 970 mg of the unreacted oily D-3,4-dimethoxy-α-methylphenyl alanine amide having a specific optical rotation $[\alpha]_D$ of +20.5° (c=1, methanol) was recovered.

On the other hand, the water layer after the extraction was adjusted to a pH of 2.0 by using hydrochloric acid. The resultant solution was vaporized to dryness. Thus, 980 mg of L-3,4-dimethoxy-α-methylphenyl alanine hydrochloride crystal having a specific optical rotation $[\alpha]_D$ of +5.4° (c=1, methanol) was obtained. Thereafter, the resultant crystal was dissolved in 20 ml of iso-propanol, and 2.0 ml of triethylamine and 2.0 l of acetic anhydride were added. The resultant solution was allowed to stand overnight and was concentrated under reduced pressure. The residue was dissolved in 2.0 ml of water, and the pH of the resultant solution was adjusted to 2.0 by using concentrated hydrochloric acid. The resultant solution was extracted with ethyl acetate, and the extracted ethyl acetate layer was dried and distillated under reduced pressure. Thus, 800 mg of L-N-acetyl-3,4-dimethoxy-α-methylphenyl alanine crystal having a melting point of 182° C. through 185° C. and a specific optical rotation $[\alpha]_D$ of −53.0° (c=1, methanol) was obtained.

The above-obtained specific optical rotation value is identical to that of L-N-acetyl-3,4-dimethoxy-α-methylphenyl alanine in literatures. Accordingly, it was confirmed that the resultant acetyl compound was L-acetyl compound and the 3,4-dimethoxy-α-methylphenyl alanine obtained above was also the L-isomer having an optical purity of 96.4%. Furthermore, the 3,4-dimethoxy-α-methylphenyl alanine amide recovered above was the D-isomer.

EXAMPLE 17

The washed cells of Mycobacterium avium chester (IFO-3154) prepared in the same manner as in Example 16 were washed with cold acetone. Thus, acetone dried cells were obtained.

DL-3,4-dimethoxy-α-methylphenyl alanine amide was dissolved in distilled water and substrate solutions having various concentrations listed in Table 2 below and having a pH of 7.0 were prepared.

The above-mentioned acetone dried cells were added to 10 ml of the substrate solutions in such an amount that the weight ratio of the dried cells to the substrate were 0.2. Then, the reaction was carried out at a temperature of 30° C. for 20 hours. The resultant reaction mixture was analyzed to determine the yield of L-3,4-dimethoxy-α-methylphenyl alanine by using a high speed liquid chromatograph.

The results are shown in Table 2 below.

TABLE 2

| Concentration of substrate (DL-3,4-dimethoxy-α-methylphenyl alanine amide) (% by weight) | Yield of L-3,4-dimethoxy-α-methylphenyl alanine (%) |
|---|---|
| 1 | 100 |
| 2 | 100 |
| 5 | 100 |
| 10 | 100 |
| 20 | 86 |
| 30 | 72 |
| 40 | 49 |

EXAMPLE 18

The washed cells of Mycobacterium avium chester (IFO-3154) prepared in the same manner as described in Example 16 were freeze dried.

The freeze dried cells were added to 10 ml of distilled water containing 10% by weight of DL-3,4-dimethoxy-α-methylphenyl alanine amide and having a pH of 7.5 in a weight ratio of the cells to the substrate listed in Table 3 below. The resultant mixture was incubated at a temperature of 30° C. for 20 hours. The reaction mixture was analyzed to determine the yield of L-3,4-dimethoxy-α-methylphenyl alanine by a high speed liquid chromatograph.

The results are shown in Table 3 below.

TABLE 3

| Freeze dried cells Substrate (Weight ratio) | Yield of L-3,4-dimethoxy-α-methylphenyl alanine (%) |
|---|---|
| 0.01 | 68 |
| 0.05 | 89 |
| 0.1 | 97 |
| 0.5 | 100 |
| 1.0 | 100 |

EXAMPLE 19

Fifty mg of the freeze dried cells of Mycobacterium avium chester (IFO-3154) prepared in the same manner as described in Example 18 were suspended in 5 ml of 0.2 M phosphate buffer solution having a pH of 7.0 and, then, the cells were disrupted under cooling by using a French press (20,000 psi). The resultant mixture was centrifuged under 20,000×g for 30 minutes. To 5 ml of the supernatant solution thus obtained, 100 mg of DL-3,4-dimethoxy-α-methylphenyl alanine amide was added, and the pH of the mixture was adjusted to 7.5. Thereafter, the mixture was incubated at a temperature of 30° C. for 20 hours.

The reaction mixture thus obtained was analyzed by a high speed liquid chromatograph. L-3,4-dimethoxy-α-methylphenyl alanine was obtained at a yield of 85%.

EXAMPLE 20

To 5 ml of the cell-free extract of Mycobacterium avium chester (IFO-3154) prepared in the same manner as described in Example 19, ammonium sulfate was added. The ammonium sulfate precipitate obtained at a saturation of 25% through 75% of ammonium sulfate was collected by centrifugation. Then, 5 ml of 0.2 M phosphate buffer solution containing 100 mg of DL-3,4-dimethoxy-α-methylphenyl alanine amide and having a pH of 7.5 was added thereto. The mixture was incubated at a temperature of 30° C. for 20 hours.

The reaction mixture thus obtained was analyzed by a high speed liquid chromatograph. As a result, L-3,4-dimethoxy-α-methylphenyl alanine was obtained at a yield of 58%.

EXAMPLE 21

Ten ml of the cell-free extract of Mycobacterium avium chester (IFO-3154) prepared in the same manner as in Example 19 was passed through a column having a diameter of 1.5 cm and a height of 65 cm and packed with Sephadex G-75. Thus, fractions having the enzyme activity were collected. These fractions were concentrated by using a semipermeable membrane method to a volume of 5 ml.

Thereafter, 100 mg of DL-3,4-dimethoxy-α-methylphenyl alanine amide was added thereto. The mixture was incubated at a temperature of 30° C. for 20 hours.

The reaction mixture was analyzed by a high speed liquid chromatograph. As a result, L-3,4-dimethoxy-α-methylphenyl alanine was obtained at a yield of 48%.

EXAMPLE 22

The washed cells (corresponding to 1.0 g of the freeze dried cells) of Mycobacterium avium chester (IFO-3154) prepared in the same manner as in Example 16 were suspended in 15 ml of 0.1 M phosphate buffer solution having a pH of 7.0 and, then, 3.75 g of acrylamide monomer, 0.2 g of N,N'-methylene bisacrylamide (i.e., crosslinking agent), 2.5 ml of a 5% aqueous 3-dime-thylamino propionitrile solution (i.e., polymerization promotor), and 2.5 ml of aqueous potassium persulfate solution (i.e., polymerization initiator) were added and mixed with one another. The mixture was allowed to stand at a temperature of 25° C. for 1 hour. Thus, the gellation of the mixture was completed.

The gel thus obtained was crushed and washed with water. The resultant immobilized product (i.e., gel particles having a particle diameter of 0.2 through 0.5 mm) was packed into a column having a diameter of 2 cm and a height of 50 cm. Thereafter, distilled water containing 10% by weight of DL-3,4-dimethoxy-α-methylphenyl alanine amide and having a pH of 7.5 was passed through the column at a temperature of 30° C. from the top of the column at a space velocity (SV) of 0.2/hr.

In this continuous reaction, the yield of L-3,4-dimethoxy-α-methylphenyl alanine was maintained at 85% or more until the reaction time became 200 hours.

EXAMPLES 23 THROUGH 25

One hundred mg of the freeze dried cells of Pseudomonas iodinum (IFO-3558) prepared in the same manner as described in Example 18 were suspended in 50 ml of 0.1 M phosphate buffer solution having a pH of 7.5. Various DL-3,4-dihydroxy-α-methylphenyl alanine amides were added to the resultant suspension and the incubation was carried out at a temperature of 30° C. for 20 hours. After removing the cells, the yields of the resultant L-3,4-dihydroxy-α-methylphenyl alanines were determined by means of a high speed liquid chromatograph.

The unreacted D-3,4-dihydroxy-α-methylphenyl alanine amides were recovered from the reaction mixtures according to the same method as described in Example 16. The L-3,4-dihydroxy-α-methylphenyl alanines thus obtained were isolated.

The results thus obtained are shown in Table 4 below.

TABLE 4

| Example No. | Substrate | Product Chemical name | Yield % | Specific optical rotation |
|---|---|---|---|---|
| 23 | DL-3,4-dihydroxy-α-methyl-phenyl alanine amide | L-3,4-dihydroxy-α-methylphenyl alanine | 83 | $[\alpha]_D$ −4.5° (c = 2, 0.1 N HCl) |
| 24 | DL-4-hydroxy-3-methoxy-α-methyl-phenyl alanine amide | L-4-hydroxy-3-methoxy-α-methylphenyl alanine | 92 | $[\alpha]_D$ +159° (c = 0.5, 0.25 M CuSO$_4$) |
| 25 | DL-3,4-methylene-dioxy-α-methyl-phenyl alanine amide | L-3,4-methylene-dioxy-α-methyl-phenyl alanine | 94 | $[\alpha]_D$ +22.0° (c = 1, 0.1 N HCl) |

We claim:
1. A process for preparing an L-α-methylphenyl alanine having the general formula: [T]

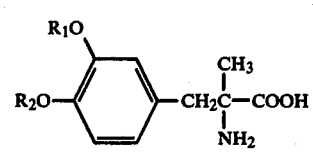

[I]

wherein $R_1$ and $R_2$ may be independently a hydrogen atom or lower alkyl groups, or $R_1$ and $R_2$ may be alkylene groups combined together to form 5 through 8-membered rings comprising the steps of:
(a) interacting a DL-α-methylphenyl alanine amide having the general formula: [II]

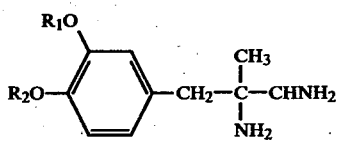

wherein $R_1$ and $R_2$ are the same as defined above, with (i) a cultivation mixture of a microorganism capable of producing an enzyme catalyzing the hydrolysis of L-isomer of DL-α-methylphenyl alanine amides (ii) a culture broth or cells separated from the cultivation mixture, (iii) the enzyme isolated from the culture broth or cells, or (iv) immobilized preparation of the cultivation mixture, whereby assymmetric hydrolysis of an L-α-methylphenyl alanine amide is effected; and (b) separating the resultant L-α-methylphenyl alanines from the hydrolysis mixture.

2. A process as claimed in claim 1, wherein said microorganism is at least one selected from the group consisting of genera Trichoderma, Rhodotorula, Nocardia, Mycobacterium, Bacillus, Rhizopus, Candida, Hansenula, Streptomyces, Aerobacter, Arthrobacter, Pseudomonas, Gibberella, Torulopsis, Enterobacter, and Ustilago.

3. A process as claimed in claim 1, wherein the reaction temperature of the asymmetric hydrolysis of L-α-methylphenyl alanine amides is within the range of from 20° C. to 50° C.

4. A process as claimed in claim 1, wherein the reaction time of the asymmetric hydrolysis of L-α-methylphenyl alanine amides is within the range of from 5 through 50 hours.

5. A process as claimed in claim 1, wherein the amount of the microorganism is in a weight ratio of from 0.01 through 2, in terms of the freeze dried cells, based on the weight of the DL-α-methylphenyl alanine amides.

* * * * *